United States Patent [19]

Wierenga et al.

[11] Patent Number: 5,399,296

[45] Date of Patent: Mar. 21, 1995

[54] SOLID COMPOSITIONS CONTAINING AMINE OXIDE-MALEIC ACID SALTS

[75] Inventors: Thomas J. Wierenga, Cincinnati; Raymond D. Young, West Chester, both of Ohio

[73] Assignee: The Procter & Gamble Company, Cincinnati, Ohio

[21] Appl. No.: 231,417

[22] Filed: Apr. 22, 1994

[51] Int. Cl.⁶ .................. C11D 1/75; C11D 3/20; C07C 59/245; C07C 291/00
[52] U.S. Cl. .................. 252/547; 252/546; 252/174.19; 564/298; 562/582
[58] Field of Search ............ 252/547, 546, 174.19; 564/298; 562/582

[56] References Cited

U.S. PATENT DOCUMENTS

| | | | |
|---|---|---|---|
| 3,275,673 | 9/1966 | Barlow | 260/459 |
| 3,983,079 | 9/1976 | Spadini et al. | 252/545 |
| 4,320,033 | 3/1982 | Yoshikawa | 252/547 |
| 4,338,216 | 7/1982 | Earl et al. | 252/311 |
| 5,075,501 | 12/1991 | Borland et al. | 564/297 |
| 5,130,488 | 7/1992 | Smith et al. | 564/298 |

OTHER PUBLICATIONS

English Abstract of Japan Patent Document JP 4904282, Apr. 18, 1974, Derwent Publications Ltd., Derwent data base accession No. 74942V/43.

*Primary Examiner*—Paul Lieberman
*Assistant Examiner*—Erin M. Higgins
*Attorney, Agent, or Firm*—William J. Winter; Rose Ann Dabek

[57] ABSTRACT

Disclosed are solid, concentrated, amine oxide surfactant compositions containing amine oxide- maleic acid salts. The molar ratio of maleic acid to amine oxide in such salts is about a 1:1. The salts are soluble in water at 25° C. at a pH of above the pKa of the amine oxide. Also disclosed is a process for preparing such solid amine oxide surfactant compositions, which process comprises admixing maleic acid and amine oxide surfactants in at least about a 1:1 molar ratio, at a pH of at least about 1 units less than the pKa of the amine oxide, to thereby form a visible precipitate therein. The precipitate is separated from the mixture, preferably by mechanical means, and dried. The dried precipitate is a maleic acid-amine oxide salt which can be incorporated into cleaning products, especially solid or granular cleaning products, as a solid, concentrated source of amine oxide surfactant.

6 Claims, No Drawings

SOLID COMPOSITIONS CONTAINING AMINE OXIDE-MALEIC ACID SALTS

TECHNICAL FIELD

The present invention relates to solid compositions containing amine oxide- maleic acid salts. Such compositions are a source of solid, concentrated amine oxide surfactants for incorporation into cleaning products, especially solid or granular cleaning products.

BACKGROUND OF THE INVENTION

Amine oxides are commonly used in cleaning compositions to boost and maintain suds formation. Such compositions include, for example, laundry, shampoo and dish washing detergent compositions.

Many methods for preparing amine oxide surfactants from the corresponding tertiary amine are known. Such methods involve the conversion of a tertiary amine in the presence of a strong oxidizing agent to the corresponding amine oxide. For example, tertiary amines can be reacted with hydrogen peroxide to yield a 30-40% aqueous solution of the corresponding amine oxide. Catalysts are commonly used to facilitate the reaction. Most of these methods, however, result in aqueous liquid formulations containing the amine oxide.

For shipping economy and for use in solid or granular detergent compositions, solid amine oxide surfactant formulations are more desirable than typical liquid amine oxide surfactant formulations. However, preparing such solid formulations has proven difficult over the years to the extent that most, if not all, of the commercially available amine oxide surfactant compositions are still in an aqueous liquid form. Such liquid formulations normally contain between 20-40% by weight of amine oxide and remain the primary source of amine oxide surfactants for use by manufacturers. It is not practical to evaporate or agglomerate these liquid formulations to obtain the solid amine oxides therein since such evaporation or agglomeration methods will result in pasty hydrates which are difficult to handle with conventional pumps and processing equipment. Spray drying the liquid formulations to obtain solid amine oxides is likewise undesirable in that the amine oxides steam distill thus forming unacceptable plume opacities during the spray drying operation.

There have been many attempts at preparing amine oxide surfactants in solid or granular formulations. One such method involves forming an aqueous solution of a salt of an amine oxide and an acid which is either an organic sulfonic acid or a fatty alcohol half-ester of sulfuric acid, and extracting the resulting salt from the solution with a water-immiscible organic solvent. Removal of the organic solvent from the resulting extract yields a dry and anhydrous amine oxide salt. Organic solvents for use in such a method can include methylene chloride, chloroform, methyl acetate, ethyl acetate, isopropyl acetate, methyl propionate, ethyl propionate, diethyl ether, dipropyl ether, ethyl propyl ether, ethyl butyl ether and methyl butyl ether. Another method for preparing amine oxide surfactants in a dry formulation involves preparing an amine oxide formulation wherein at least some of the amine oxide is in dihydrate form. In accordance with such a method, the amine oxide is formed by reacting a concentrated aqueous hydrogen peroxide with a tertiary amine in a reaction mixture which is maintained stirrable throughout the reaction by the use of an organic solvent which solubilizes the reaction mixture at the reaction temperature but permits precipitation of the resulting amine oxide at a lower temperature. After the reaction, solvent temperatures are reduced to induce amine oxide precipitation.

These methods for preparing amine oxide surfactants in solid formulations typically involve the use of organic solvents to induce precipitation of the amine oxide, or to otherwise control its solubility. However, the use of organic solvents in this manner has some serious disadvantages. First, the organic solvent must eventually be removed from the amine oxide material in an additional manufacturing step. Secondly, reducing the level of organic solvent residuals to an acceptable level in the amine oxide material can be difficult or economically unfeasible.

The foregoing considerations involving amine oxide surfactant formulations and the processes for preparing them indicate that there is a continuing need to provide solid formulations containing amine oxide surfactants. Accordingly, it is an object of the present invention to provide a solid, concentrated composition containing amine oxide- maleic acid salts, which salts can be used as a source of amine oxide surfactants in cleaning compositions.

SUMMARY OF THE INVENTION

The present invention is directed to solid amine oxide compositions which are useful in formulating cleaning products, especially solid or granular cleaning products. These solid compositions consist of amine oxide- maleic acid salts, wherein the maleic acid and amine oxide in the formed salt are in about a 1:1 molar ratio and are soluble in water at 25° C. at a pH of above the pKa of the amine oxide.

The solid compositions of the present invention are prepared by a process comprising admixing maleic acid with an aqueous liquid amine oxide surfactant formulation in at least about a 1:1 molar ratio and at a pH of at least about 1 unit below the pKa of the amine oxide, to thereby form a visible precipitate in the admixture. The formed precipitate is separated from the admixture, preferably by mechanical means, and allowed to dry. The separated precipitate forms the solid compositions of the present invention, which solid compositions consist of the maleic acid-amine oxide salts described herein.

DETAILED DESCRIPTION OF THE INVENTION

As used herein, "aqueous liquid amine oxide formulations" are liquid compositions typically comprising from about 1% to about 50% by weight of amine oxide surfactant in water.

As used herein, the term "solid compositions" mean particulate (e.g., powders, granules, agglomerates) and non-particulate solids.

As used herein, all pKa and pH values are measured in water at 25° C.

As used herein, all percentages, parts and ratios are based on weight unless otherwise specified.

As used herein, the term "comprising" means various components can be conjointly employed in the solid composition of the present invention. Accordingly, the terms "consisting essentially of" and "consisting of" are embodied in the term comprising.

The solid compositions of the present invention and a process for preparing them, including preferred embodiments thereof, are described in detail as follows.

Aqueous Liquid Amine Oxide Formulations

Aqueous liquid amine oxide formulations for use in the process herein are aqueous liquids comprising varying amounts of amine oxide surfactant therein. Such aqueous liquid amine oxide formulations, and the processes for preparing them, are well known in the surfactant art.

The aqueous liquid amine oxide formulations for use in the instant process comprise varying percentages of amine oxide surfactant. The percentage of amine oxide surfactant in the liquid formulation, as well as the type of such amine oxide surfactant, are not critical to the successful operation of the instant process. Accordingly, any known or conventional aqueous amine oxide formulation can be used. Such known or conventional formulations typically contain up to about 50%, more typically from about 20% to about 40%, by weight of amine oxide surfactant. It is understood, however, that formulations containing higher and lower concentrations of amine oxide surfactant can also be used in the instant process. More concentrated formulations are preferred from a manufacturing cost standpoint.

The remainder of the aqueous amine oxide formulations for use in the process herein will typically, and preferably, be water. Less preferred are single phase mixtures of water and water-miscible solvents.

Amine oxide surfactants for use in the instant process preferably have the formula RR'R"NO, where R is a substituted or unsubstituted alkyl or alkenyl group containing from about 8 to about 30, preferably about 8 to about 18, carbon atoms. Groups R' and R" are each substituted or unsubstituted alkyl or alkenyl groups containing from about 1 to about 18, preferably from about 1 to about 4, carbon atoms. More preferably, R' and R" are each methyl groups, examples of which include dodecyldimethyl amine oxide, tetradecyldimethyl amine oxide, hexadecyldimethyl amine oxide, octadecyldimethyl amine oxide, and coconutalkyldimethyl amine oxides.

Examples of suitable amine oxide surfactants for use in the instant process include, but are not limited to, dodecyldimethyl amine oxide, tridecyldimethyl amine oxide, tetradecyldi-methyl amine oxide, pentadecyldimethyl amine oxide, hexadecyldimethyl amine oxide, heptadecyldimethyl amine oxide, octadecyldimethyl amine oxide, dodecyldiethyl amine oxide, tetradecyldimethyl amine oxide, hexadecyldiethyl amine oxide, octadecyldiethyl amine oxide, dodecyldipropyl amine oxide, tetradecyldipropyl amine oxide, hexadecyldipropyl amine oxide, octadecyldipropyl amine oxide, dodecyldibutyl amine oxide, tetradecyldibutyl amine oxide, hexadecyldibutyl amine oxide, octadecyldibutyl amine oxide, dodecylmethylethyl amine oxide, tetradecylethylpropyl amine oxide, hexadecylpro-pylbutyl amine oxide, and octadecylmethylbutyl amine oxide.

Also useful are amine oxide surfactants made by the oxidation of tertiary amines prepared from mixed alcohols obtainable from coconut oil. Such coconutalkyl amine oxides are preferred from an economic standpoint inasmuch as it is not necessary for the present purposes, to separate the mixed alcohol fractions into their pure components to secure the pure chain length fractions of the amine oxides.

Aqueous liquid amine oxide formulations for use in the instant process can be prepared by known and conventional methods. Such methods normally involve the controlled oxidation of tertiary amines to the corresponding amine oxide using a strong oxidizing agent. A preferred oxidizing agent is hydrogen peroxide. A dilute, or, preferably, concentrated (30% by weight or more) hydrogen peroxide solution is added in a stochiometric or greater amount to an aqueous solution containing the tertiary amine for conversion thereof to the amine oxide. Reaction rates and amine oxide yields can be improved by incorporation of catalysts and or chelating agents well known in the surfactant art for this particular application. Methods for making amine oxide surfactants are described, for example, in U.S. Pat. No. 3,215,741, U.S. Pat. No. 3,223,647, British Patent 437,566, and U.S. Pat. No. 4,565,891.

All such known or conventional methods for preparing amine oxide surfactants typically result in aqueous liquid formulations. As described hereinafter, it is from these aqueous liquid formulations that the maleic acid-amine oxide salts disclosed herein are ultimately formed.

Maleic Acid (Cis-Butenedioic Acid)

The process for preparing the solid compositions of the present invention involves admixing maleic acid with the aqueous liquid amine oxide formulation described hereinbefore. It was found that among carboxyl-containing compounds, including mono-, di- and poly- carboxylates, only maleic acid will effectively precipitate amine oxide surfactants from the aqueous liquid amine oxide formulations. As used herein, the term "carboxylates" means carboxyl-containing compounds generally.

Known or conventional sources of maleic acid can be used in the process herein. Maleic acid is readily available, for example, as a white, crystalline particulate that can be added directly to an aqueous liquid amine oxide formulation in accordance with the instant process. Maleic acid is well known for use in dying and finishing of cotton, wool and silk, as a preservative in fats and oils, and for use in synthesizing various other organic compounds. Polycarboxylates such as maleic acid can also act as detergent builders. Maleic acid is typically available as a colorless, water soluble, crystalline solid.

An essential step of the instant process includes adding maleic acid in the requisite amounts to an aqueous liquid amine oxide formulation. The form in which the maleic acid is added to such a formulation is not critical to the instant process. For example, the maleic acid can be added as a crystalline particulate, or as a dissolved or suspended particulate in a carrier liquid. Preferably, such a carrier liquid is water.

Water soluble salts of maleic acid can also be used in the instant process. Such salts can comprise alkali metals (e.g., sodium, potassium), alkali earth metals, ammonium, substituted ammonium, and so forth. Preferred among such salts are sodium and potassium maleate. Other water soluble maleate salts can also be used in the instant process provided that such salts are compatible with the amine oxide surfactant selected for use herein.

pH adjustment of the aqueous liquid amine oxide formulation to the requisite level ( at least about 1 unit below the pKa of the amine oxide surfactant) is normally needed when maleate salts are used in the instant process. Such pH adjustment is not necessary, however, when maleic acid is used since admixtures of maleic acid and aqueous amine oxide formulations will inherently have pH values at least about 1 unit below the pKa of most amine oxide surfactants. Precipitation of the desired amine oxide salt will not occur to any large extend until such admixture pH values are realized.

The instant process is described herein in terms of the addition of maleic acid to an aqueous amine oxide formulation. It is understood, however, that any reference herein to maleic acid implicitly includes maleate salts (described hereinbefore), maleic acid and mixtures thereof.

As described hereinafter, among carboxyl-containing compounds, it was found that only maleic acid formed an acceptable yield of insoluble amine oxide salts (e.g., insoluble at pH values below the pKa of the selected amine oxide surfactant) when utilized in the instant process.

Process

A process for preparing the solid compositions of the present invention comprises admixing maleic acid and an aqueous liquid amine oxide formulation to form a visible precipitate therein, and then separating the formed precipitate from the admixture. The process is described in detail as follows.

In a first step of the process, maleic acid and the aqueous liquid amine oxide formulation described herein are admixed in a molar ratio (maleic acid to amine oxide surfactant) of at least about 1:1, to form an admixture having a pH of at least about 1 unit below the pKa of the amine oxide surfactant. Such pKa values for the selected amine oxide surfactants are easily determined by one skilled in the chemical arts. Although higher molar ratios can be used, a molar ratio of about 1:1 is preferred. Molar ratios less than 1:1 will not result in the desired degree of salt precipitation. As stated hereinbefore, the maleic acid can be admixed directly into the aqueous liquid amine oxide formulation as, for example, a crystalline solid or as dissolved or suspended solids in a liquid carrier. The aqueous amine oxide formulation will of course be in liquid form as described hereinbefore.

If necessary, e.g., when maleate salts are used, the pH of the amine oxide-maleate admixture is decreased until a visible precipitate forms in the admixture. These pH adjustments can also be made prior to, during, or after the admixing step. The desired precipitation will occur only when the admixture pH decreases to least about 1 unit less than the pKa of the amine oxide surfactant (pKa 4–6), at which point a significant portion (e.g., >90%) of the amine oxide surfactant becomes protonated and forms an insoluble salt with the maleic acid in the admixture. If and when such pH adjustments are performed, the means for making the adjustments are well within the skill of one in the chemical arts.

The formed precipitate made in accordance with the instant process is an amine oxide- maleic acid salt.

In a second step of the instant process, the formed precipitate is separated from the admixture. Preferably, such separation is accomplished by mechanical means such as screening, filtering, centrifuging and the like. The separated precipitate can then be washed with cold water (pH adjusted to about the pKa of the amine oxide) to remove unprecipitated reactants, and then dried to form a solid composition of the present invention. The solid composition thus formed can be reduced to fine particles, agglomerated, and so forth.

Since the formed precipitate can be separated by mechanical means, there is no need to use organic extraction solvents to perform such separations. It is understood, however, that the use of organic extraction solvents can be used in the instant process but that their use is neither preferred nor necessary. Water of hydration of the formed complex will vary depending on the drying operation utilized, e.g., air drying, forced air drying, convection hot air drying, organic solvent drying/washing, and so forth.

Product

The solid compositions of the present invention, prepared in accordance with the process described hereinbefore, is a solid, concentrated source of amine oxide surfactant for use in cleaning products.

The solid compositions of the present invention consist of maleic acid-amine oxide salts prepared in accordance with the above described process. The type of amine oxide surfactants suitable for incorporation into such maleic acid-amine oxide salts are described hereinbefore. The molar ratio of maleic acid to amine oxide in the formed salt is about 1:1. These formed salts have a melting point (m.p.) of less than 100° C. and appear as fine, white particulates, e.g., powders, granules, agglomerates.

The solid compositions of the present invention can be incorporated into cleaning products, especially solid or granular cleaning products, where the incorporation of a liquid amine oxide formulation would be difficult. When such cleaning products are added to or contacted with water at a pH above the pKa of the amine oxide surfactant (typically above from about 4 to about 6, more typically about 5), the maleic acid- amine oxide salt goes into solution thus delivering amine oxide surfactant and maleic acid to the reconstituted product. The amine oxide surfactant thus released into solution can provide suds boosting and maintenance to the cleaning products. It can also act as a primary surfactant. The maleic acid, like many other polycarboxylates, can provide detergency building characteristics to the cleaning product.

Comparative Data

The following test was performed to show the importance of using only a specific carboxylate-containing compound, maleic acid, in the solid compositions of the present invention. Various carboxyl-containing compounds were admixed with 100 ml samples of $C_{9-15}$ alkyldimethyl amine oxide (31% by weight amine oxide in water) in at least about a 1:1 molar ratio of the carboxyl-containing compound to the amine oxide. If necessary, the pH of each admixture was then adjusted with a 6 N hydrochloric acid solution to about 1 unit below the pKa of the amine oxide (e.g., about 4.5 for an amine oxide with a pKa of about 5.5) in an attempt to induce precipitate formation. Each admixture was visually observed for precipitate formation. Results are set forth in Table 1.

TABLE 1

| Formulation | Carboxylate | Solution pH | Visible precipitate |
|---|---|---|---|
| A | Maleic acid (pKa 2.0, 6.26) | 4.5 | yes-immediate |
| B | Fumaric acid (pKa 3.1, 4.6) | 3.5–5.5 | no |
| C | Succinic acid (pKa 4.19, 5.57) | 4.5 | no |

TABLE 1-continued

| Formulation | Carboxylate | Solution pH | Visible precipitate |
|---|---|---|---|
| D | Phthalic acid (pKa 4.2, 5.6) | 4.5 | slight |
| E | Polyacrylic acid (avg M.W. 2,000) (pKa 4.26-acrylic acid) | 4.5 | no |

It can be seen from the data in Table 1 that only maleic acid formed the desired amine oxide salt in an acceptable yield (e.g. about 100% amine oxide precipitated). Phthalic acid formed a slight precipitate with the amine oxide but most (e.g., 85–95%) of the amine oxide remained unprecipitated. None of the other carboxylates formed a precipitate with the amine oxide surfactant.

EXAMPLES

The following includes specific embodiments of the solid compositions of the present invention. These embodiments are illustrative of the invention and are not intended to be limiting of it.

Example 1

About 15.3 grams of maleic acid crystals are admixed with about 100ml of an amine oxide solution ($C_{9-15}$ alkyldimethyl amine oxide, 31% active in water). The molar ratio of maleic acid to active amine oxide is about 1:1. The pH of the solution is adjusted as needed with either 6N hydrochloric acid or 50% NaOH solution to about 4.5 (below about the pKa of the amine oxide). A visible precipitate forms almost immediately. The admixture is allowed to set for about 5 minutes. The precipitate is then filtered from the admixture, washed with cold water (pH 4.0), and air dried before it is reduced to a fine powder.

Analysis of the resulting powder shows a maleic acid-amine oxide salt in a 1:1 molar ratio of maleic acid to amine oxide in the formed salt. The amine oxide moiety in the formed salt is a $C_{9-15}$ alkyldimethyl amine oxide. The formed salt is water soluble at 25° C. at a pH of about 5.5.

Example 2

The process described in Example 1 is repeated except that a different amine oxide solution is employed-Ammonyl LO ($C_{12}$ dimethyl amine oxide, 30% active in water, Stepan Company, Northfield, Ill.). Results are the same as in Example 1 but with a different amine oxide moiety ($C_{12}$ dimethyl amine oxide) in the formed salt. The formed salt is water soluble at 25° C. at a pH of about 5.5.

Example 3

The process described in Example 1 is repeated except that a different amine oxide solution is employed-Varox 1770 (Cocoamido propyl amine oxide, 35% active in water, Witco/Sherex, Dublin, Ohio). Results are the same as in Example 1 but with a different amine oxide moiety (cocoamidopropyl amine oxide) in the formed salt. The formed salt is water soluble at 25° C. at a pH of about 5.5.

What is claimed is:

1. Solid amine oxide surfactant compositions, comprising:
   maleic acid-amine oxide salts, wherein the molar ratio of maleic acid to amine oxide in the salt is about 1:1, and wherein the maleic acid-amine oxide salt is soluble in water at 25° C. at a pH of above about the pKa of the amine oxide surfactant.

2. A solid amine oxide surfactant composition according to claim 1 wherein the amine oxide has the formula RR'R"NO, where R is selected from the group consisting of substituted and unsubstituted alkyl and alkenyl groups containing from about 8 to about 30 carbon atoms, where R' and R" are each selected from the group of substituted and unsubstituted alkyl and alkene groups containing from 1 to about 18 carbon atoms.

3. A solid amine oxide surfactant composition according to claim 2 wherein the R group on the amine oxide contains from about 8 to about 18 carbon atoms, and the R' and R" groups each contain from about 1 to about 4 carbon atoms.

4. A solid amine oxide surfactant composition according to claim 3 wherein R' and R" are each methyl groups.

5. A solid amine oxide surfactant composition according to claim 4 wherein the amine oxide is selected from the group of dodecyldimethyl amine oxide, tetradecyldimethyl amine oxide, hexadecyldimethyl amine oxide, octadecyldimethyl amine oxide, coconutalkyldimethyl amine oxide and mixtures thereof.

6. A solid amine oxide surfactant composition according to claim 1 wherein said composition is solid particulate composition.

* * * * *